United States Patent [19]
Richter

[11] Patent Number: 5,840,022
[45] Date of Patent: *Nov. 24, 1998

[54] METHOD FOR IMAGING DISPLAY OF A PART OF THE HUMAN BODY

[75] Inventor: Kari Richter, Berlin, Germany

[73] Assignee: Siemens Aktiengesellschaft, Munich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 530,364

[22] PCT Filed: Mar. 18, 1994

[86] PCT No.: PCT/DE94/00301

§ 371 Date: Sep. 22, 1995

§ 102(e) Date: Sep. 22, 1995

[87] PCT Pub. No.: WO94/21189

PCT Pub. Date: Sep. 29, 1994

[30] Foreign Application Priority Data

Mar. 22, 1993 [DE] Germany .......................... 43 09 597.6

[51] Int. Cl.⁶ ....................................................... A61B 5/05
[52] U.S. Cl. .......................... 600/407; 128/915; 378/37; 378/63
[58] Field of Search ................................ 128/653.1, 915, 128/660.01, 660.07, 736, 742; 378/37, 62, 63; 600/407, 437, 443, 549, 555

[56] References Cited

U.S. PATENT DOCUMENTS

| | | |
|---|---|---|
| 4,075,883 | 2/1978 | Glover . |
| 4,407,163 | 10/1983 | Hundt et al. ........................ 128/660.07 |
| 4,509,368 | 4/1985 | Whiting et al. . |
| 4,543,959 | 10/1985 | Sepponen . |
| 4,651,744 | 3/1987 | Bristov et al. . |
| 4,936,291 | 6/1990 | Forssmann et al. . |
| 5,146,924 | 9/1992 | Sepponen . |
| 5,361,767 | 11/1994 | Yukov ................................ 128/660.06 |
| 5,398,684 | 3/1995 | Hardy .................................. 128/653.1 |
| 5,474,072 | 12/1995 | Shmulewitz ............................. 128/915 |

FOREIGN PATENT DOCUMENTS

| | | |
|---|---|---|
| 0 570 936 | 11/1993 | European Pat. Off. . |
| 2 545 349 | 5/1993 | France . |
| 40 21 102 | 1/1991 | Germany . |
| 40 37 387 | 5/1992 | Germany . |
| 55-145461 | 1/1980 | Japan . |
| 58-32432 | 3/1983 | Japan . |
| 59-45112 | 3/1984 | Japan . |
| WO 83/02053 | 6/1983 | WIPO . |
| WO88/08272 | 3/1988 | WIPO . |
| WO 8808272 | 11/1988 | WIPO . |

OTHER PUBLICATIONS

"Adaption, Development and Expansion of Xray Mammography Techniques for Ultrasound Mammography," Kelly-Fry, J. Ultrasound Med. 10:S1–S104, Mar. 1991.

"Breast Cancer Detection with Sonography and Mammography: Comparison Using State-of-the-Art Equipment," Sickles et al., Am. J. Roentgenlogy, vol. 140, May 1983, pp. 843–845.

*Primary Examiner*—Brian L. Casler
*Attorney, Agent, or Firm*—Hill & Simpson

[57] ABSTRACT

In a method and apparatus for displaying an image, particularly of the female mammary gland, obtained from echo signals produced by ultrasound radiation directed onto the subject, the evaluation of echo signals time-dependently received by an echo signal receiver ensues on a subject axis directed in the spatial direction of the primary radiation and the intensity of the echo signals is evaluated. In the imaging evaluation, the echo signal is combined in a corresponding spatial reference orientation with a further imaging signal of a different signal source registered in the corresponding spatial direction with the subject held fixed in the same position as for producing the echo signals. The further imaging signal by itself, or in combination with the echo signals, provides diagnostic information not available from the echo signals by themselves. In the case of the female mammary gland, the mammary gland is fixed between two plates directed essentially parallel.

20 Claims, 5 Drawing Sheets

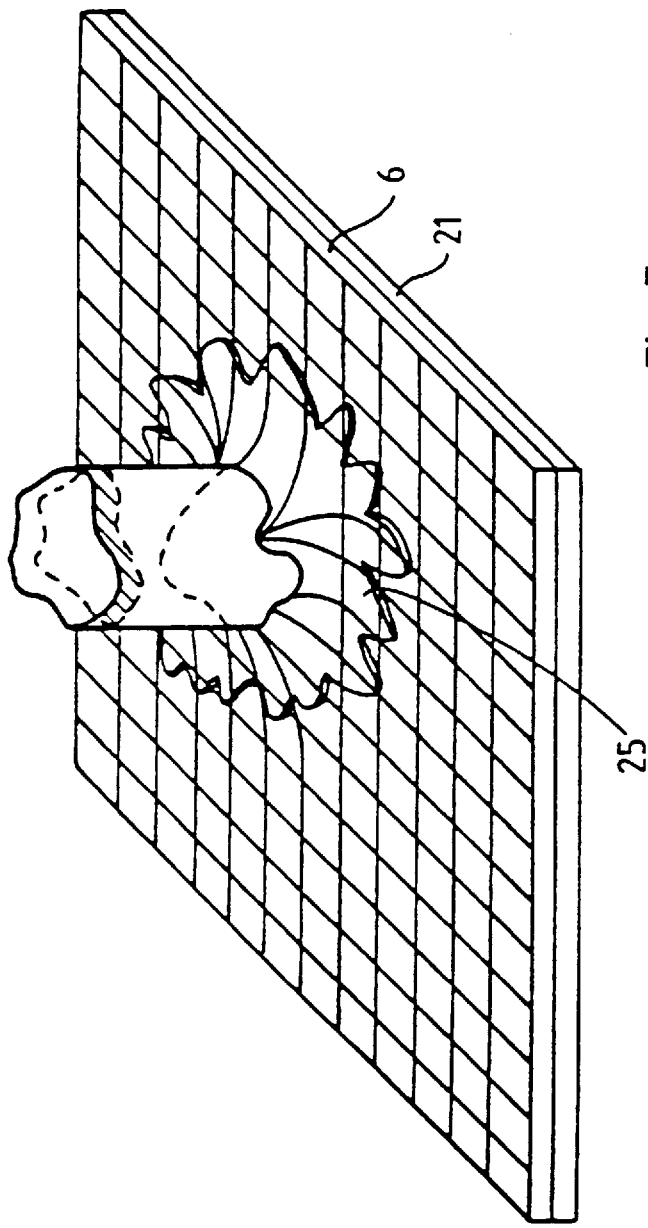

METHOD FOR IMAGING DISPLAY OF A PART OF THE HUMAN BODY

BACKGROUND OF THE INVENTION

1. Field of the Invention

The present invention is directed to a method and apparatus for conducting an examination of a subject, such as a mammography apparatus and method, wherein an image is obtained by introducing ultrasound into the subject and recording the resulting ultrasound echo signals.

2. Description of the Prior Art

Ultrasound imaging is increasingly utilized as screening examinations of body portions in cancer prevention.

The regular precautionary examination of the female mammary gland for early detection of breast cancer is extremely desirable since this illness, which represents the most common type of cancer in women in industrialized countries, has a significant tendency to spread and an early detection of the sickness usually means a cure. X-ray mammography is thereby an established method and is implemented in most instances by displaying the breast in two planes oriented perpendicularly to one another.

Ultrasound examinations represent a non-hazardous mammographic examination method and even extremely dense gland tissue (mastopathy) does not represent a problem since the tumors in dense gland tissue are visible in a sonographic display. X-ray mammography, by contrast, has no diagnostic value given patients with a mastopathy or with endoprotheses in the breast region since the tumors can then not be displayed or can only be poorly displayed.

An ultrasound tomograph disclosed by U.S. Pat. No. 4,509,368 operates according in the manner described above. Therein, signals that are acquired reflection and transmission in the examination subject are superimposed on one another. The spatial directions of the reflected and transmitted signals thereby reside perpendicular to one another. Although this arrangement enables a gain in information compared to known solutions, systems operating according to this method have been employed in practice in significant numbers. This is because the apparatus is relatively complicated in structure and a number of acoustic transmitters and acoustic receivers are required, as a result of which the apparatus is expensive and is also not simple in terms of manipulation.

Further, German OS 40 37 387 discloses a method wherein the echo values obtained for coinciding spatial points from radiation directions opposite one another are superimposed, so that signal parts ultimately remain only for those spatial points that deviate from one another dependent on the radiation direction. As a result, information with respect to the shape and the surface structure of a recognized inhomogeneity can be derived better, since acoustic occlusions and the like are eliminated. It is still a disadvantage of this method, however, that the part of the body to be examined must be examined from two opposite spatial directions, so that the acoustic applicator head must either be shifted in position or, two acoustic heads are necessary.

PCT Application WO 88/08272 discloses a method and an apparatus for examining the female breast by means of serial examinations for cancer detection. The apparatus has an infrared radiation source with which the tissue to be examined is illuminated. A video camera receives that part of the infrared radiation that has passed through the tissue. In addition, an ultrasound transducer arrangement is provided for examining a tissue region. The overall examination is thus a two-stage examination procedure. Suspicious regions are identified by the aforementioned diaphanography procedure a designational examination with the ultrasound Doppler method subsequently ensues.

In a method disclosed by U.S. Pat. No. 4,651,744, it is also the goal to differentiate lesions previously detected by diaphanography with ultrasound because an ultrasound examination of the entire examination region is described therein as being too involved in order to be employed in series examinations.

European Application 0 168 559 is directed to the locating of calculi that are to be disintegrated with a lithotriptor using ultrasound shock waves. Movement of the calculus to be treated is to be recognized in real-time ultrasound images. An X-ray locating system that supplements the ultrasound locating is correlated with the ultrasound locating system. However, no direct superimposition of X-ray information and ultrasound information ensues, this being neither possible nor intended for locating.

French Patent 2 545 349 discloses an imaging method for anatomical organ structures, whereby X-ray images are overlaid with images from a different type of radiation. For example, ultrasound, infrared and magnetic resonance images are recited. Before the superimposition, the structures that are easily visible in the individual images are skeletized, this meaning that the corresponding structures are to be rendered free or bare down to the essence thereof. The picture elements of the superimposition image are taken either from the first or from the second image.

Known methods based only on ultrasound that have been introduced have not yet supplied any results that, in and of themselves, would enable adequately reliable findings in screening examinations.

SUMMARY OF THE INVENTION

It is an object of the present invention to provide a method and an apparatus for conducting an ultrasound examination of a subject for the purpose of cancer screening wherein an image is produced having a content which permits a more reliable diagnosis and which is easier for a less-experienced examining person to interpret.

The above object is achieved in accordance with the principles of the present invention in a method and in an apparatus for displaying an image of a female mammary gland using echo signals obtained by ultrasound irradiation of the mammary gland, the displayed echo signals being presented in the image dependent on their intensity along an axis in the mammary gland of the transmitted ultrasound, the echo signals being presented in the image in a spatial allocation corresponding to the source of the echo signals in the mammary gland and wherein further imaging signals are obtained by generating a different type of examining field in which the mammary gland is disposed, the further signals being obtained along the same direction as the transmitted ultrasound, with the mammary gland being held fixed between the ultrasound examination and the examination with the further examining field.

The invention is based on the perception that a significant gain in information can be achieved by the common employment of two supplementary imaging methods that, with the breast fixed, enable the direct or indirect geometrical superimposition of the imaging information, this gain in information, in particular, being greater than the sum of the information to be separately derived from the two methods. A cumulative information effect is thereby achieved because the ability to recognize an incomplete geometrical structure is significantly improved for a human observer by adding only a few additional elements.

The further signals are obtained by x-ray thermographic and/or with examination of the breast.

Preferably, methods based on ultrasound echoes and on X-ray fluoroscopy represent supplementary, i.e. complementary methods in such a way that tissue anomalies that are not clearly reproduced by the one method emerge all the better in the other method. Given direct superimposition of the images registered at the fixed subject, the imaging presentations thus supplement one another to form an image that nearly completely reproduces the malignant regions. This superimposition also improves the display of respective, individual geometrical elements or structures of the image reproduction.

A further advantage of the inventive method and apparatus is that it is only necessary to stress the breast by exposure to x-rays for the production of one image plane and two X-ray images thus no longer need to be prepared from different directions, as hitherto in X-ray mammography.

By combining the various examination methods with the breast in the same position, less ambiguous results—by contrast to earlier methods—are already possible because the image geometries previously acquired with the various methods could not be allocated to one another—because of the different organ position or appearance in the various exposure directions. Even if an ultrasound examination and an x-ray examination were undertaken in accordance with the conventional approach, these separate examinations did not supply information which could be interpreted directly in common and in combination.

It is also of significance for the inventive method that picture elements from spatial methods (ultrasound) are informationally combined with those that are acquired by shadow formation in fluoroscopy. The ultrasound method thus enables depth locating of findings which were only two-dimensionally localized by the shadow-forming methods.

In an embodiment of the invention, the different imaging methods can be activated in different stages, so that an exact discrimination can respectively ensue.

In particular, the signal obtained by X-radiation is directly digitally recorded or is subsequently digitized from an X-ray exposure obtained in a standard way.

When the signal sources—simultaneously or in chronological succession—are arranged at the same side of the subject in spatial coordination, the receiver plate for a shadowing method can be combined in a preferred way with a reflector surface for an imaging method working with echo effect.

In another preferred embodiment of the method, additional information representative of a high probability that a tumor is present at a particular location can be obtained by logical operation and/or superimposition of the further signal with the signal characteristic of a high tumor probability derived from the echo information, particularly by additive or multiplicative operation. The zones that are especially relevant for the interpretation of the examination are thereby clearly emphasized.

The primary radiation of the echo-generating signal is emitted onto the subject to be examined, in particular, continuously or as a sequence of essentially equidistant pulses onto the subject to be examined, whereby the primary radiation transmitter is mechanically driven and/or a plurality of spatially distributed primary radiation transmitters in an array are driven in chronological succession or simultaneously in scanning fashion.

In another preferred embodiment of the inventive method, the subject is located between the primary radiation transmitter/echo signal receiver and a reference surface that is aligned perpendicular to the spatial direction of the primary radiation and reflects the primary radiation more strongly as an echo signal than other regions of the body tissue located in the presentation field. The average or expected transit time and/or amplitude of an echo signal of the primary radiation passing through the object that is reflected by the reference surface and received by the primary radiation transmitter/echo signal receiver is determined or retained. The transit time and/or amplitude of an echo signal passing through the subject that is reflected by the reference surface and received by the primary radiation transmitter/echo signal receiver can be identified. The deviation of the transit time and/or amplitude of this registered echo signal reflected by the reference surface from the transit time of the reference echo signal or from the reference amplitude then forms a criterion for the tumor probability in the region of the spatial direction of the propagation of this echo signal. A maximum of imaging information that enables a closed display can be acquired in this way from the superimposed signals.

It is especially advantageous in the above-described methods that the image data that are obtained require no geometrical correction since they can be linearly superimposed without further difficulty to form an overall display.

In general form, regions of the image presentation can thereby be generated by common evaluation of echoes registered for points neighboring one another, so that a complete display of the reference plane is enabled given maximum utilization of the registered signal information.

It is also beneficial when the points or regions are superimposed to form a two-dimensional or three-dimensional graphic display, particularly a color display.

The inventive method can also be employed for a spatially imaging presentation in the fashion of computed tomography by emitting primary radiation onto the body part to be examined along a path covering the area of the body part either continuously or in an essentially equidistant succession of adjoining spatial directions.

An apparatus for the implementation of the inventive method thereby respectively has primary radiation sources and radiation receivers formed by respective signal transducers as well as a signal processor with a program memory and signal connections to the signal transducers.

Since the wave radiation scans the relevant body part, i.e. the subject to be examined, in chronological succession and a stable support, in particular, moving subjects is beneficial in this respect, the subject in the preferred embodiment of the inventive apparatus is arranged between a plate-shaped element, that is essentially transparent for the wave radiation, and the reference surface that reflects the echo signals, the element and the reference surface being aligned parallel to one another.

Because subjects to be examined can have different shapes, the element transparent for the wave radiation and the reflective reference surface are connected to one another with an axial adjustment means. The subject to be examined, surrounded by a coupling medium, is thus clamped in a fixed fashion by actuating the adjustment means after the introduction the subject between the reference surface and the element, which are likewise provided with the coupling medium, so that relatively large regions of the subject directly touch the element or the reference surface and a good coupling between subject and element or reference surface is thus guaranteed in a simple way. Since the thicknesses of the regions to be traversed by the ultrasound signal are thus defined, a transmitter/receiver having suitable focusing can be employed, so that losses in time due to mismeasurements are avoided.

The coupling medium surrounding the subject is preferably contained in a flexible container whose shape can be adapted to the shape of the subject. The container is made of a material transmissive for the wave radiation and the coupling medium is such that the speed of sound and/or the absorption of the wave radiation in the coupling medium is essentially the same as that of the wave radiation in the body tissue of the subject to be examined. As a result, those regions of the subject whose surface does not reside in immediate contact with the transmissive element or the reflective reference surface can also be examined.

In a preferred embodiment of the inventive apparatus, the ultrasound transmitter/receiver can be locked in a carriage lying against the outside surface of the plate-shaped element transmissive for the wave radiation the carriage being translationally movable such that the subject to be examined together with the reflective reference surface behind it can be scanned point-by-point in a grid in chronological succession in a simple way either manually or under motor drive. In the case of a linear or two-dimensional array arrangement, the required motion sequences are simplified or can be entirely eliminated. In an embodiment employing a two-dimensional array, this two-dimensional array itself can form the pressing surface. The drive thereby ensues in scanning fashion with a corresponding electronic circuit.

In the examination of a human body part and, in particular for the examination of the female mammary gland, the respective regions of the element transmissive for the wave radiation and the reflective reference surface body part are matched in shape thereto and, in particular, are provided with a connecting edge having a concavely shaped recess.

A preferred way of evaluating the obtained information is to produce a computer-calculated, three-dimensional display of the ultrasound-reflective reference surface on a monitor, so that the size of the region of the subject to be examined wherein there is a high probability a tumor is present can be simultaneously surveyed. The simultaneous display of the characteristic information is thus possible in a single image that can be aligned in different views by the corresponding, graphic control means of the computer.

A closer diagnosis can then ensue by selecting the display of the tissue regions belonging to (allocated to) the conspicuous regions of the reference surface. By enlargement of an image excerpt (zoom), tissue zones of interest can be separately reproduced, so that a more exact evaluation is possible.

DESCRIPTION OF THE DRAWINGS

FIG. 5 is a three-dimensional illustration of the ultrasound-reflecting surface in the ultrasound image given the existence of a tumor in the subject under examination.

DESCRIPTION OF THE PREFERRED EMBODIMENTS

Figure 1:
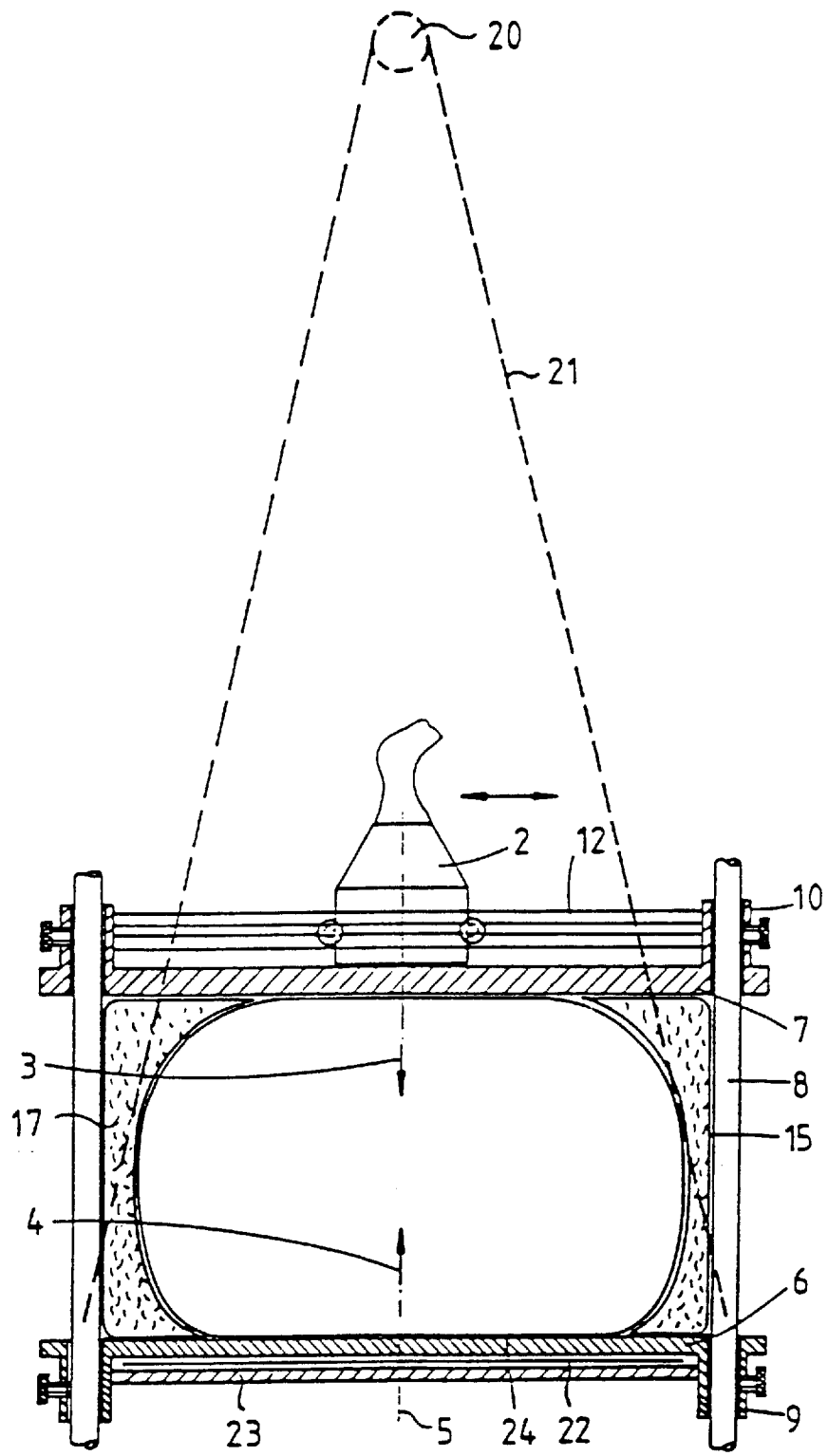
FIG. 1 illustrates the preferred embodiment of the inventive apparatus for the implementation of the inventive method, shown in section.
Figure 2:
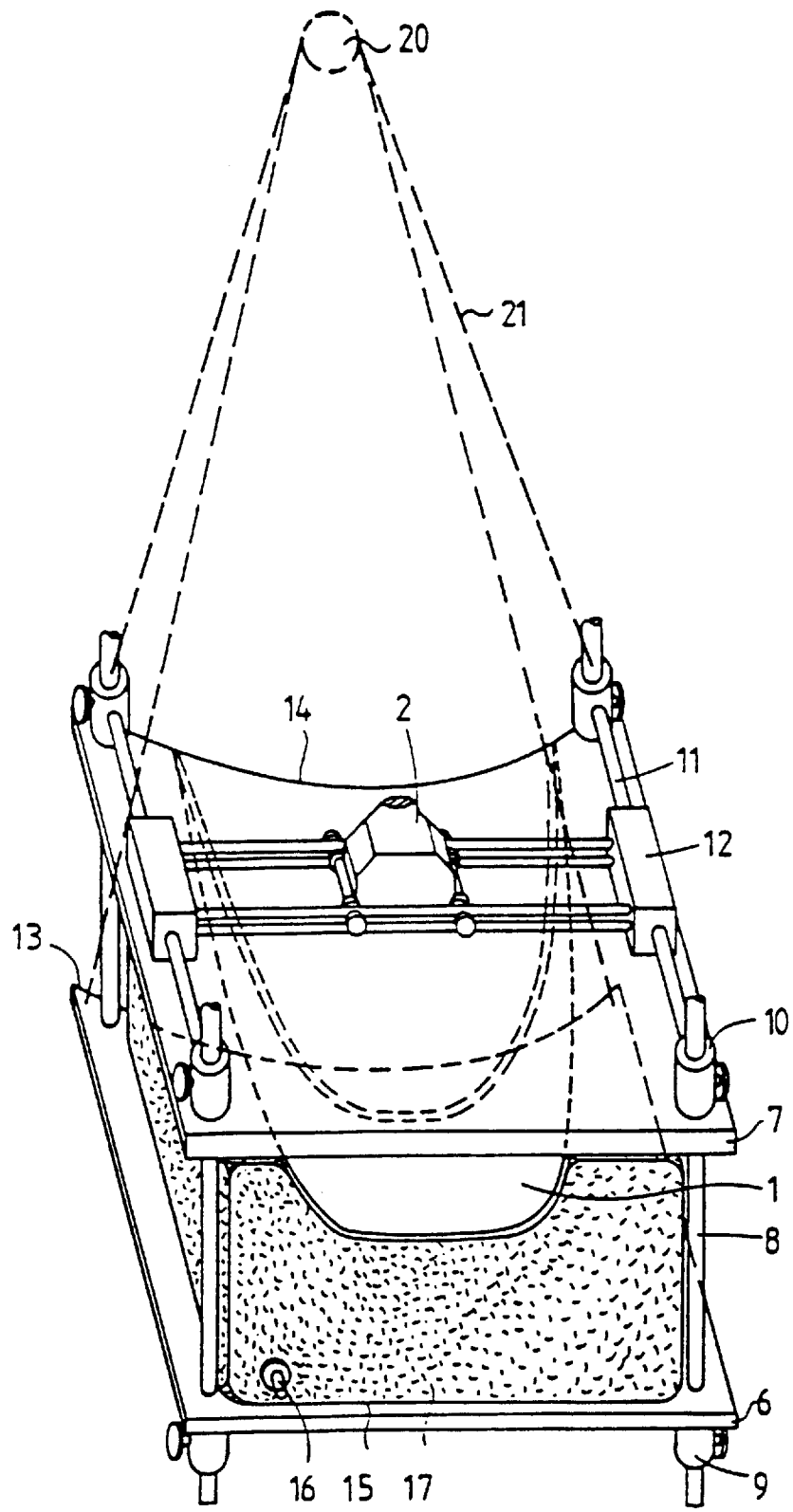
FIG. 2 illustrates the apparatus of FIG. I in a perspective view.

In the preferred embodiment of the inventive apparatus shown in a side view in FIG. 1 and in perspective in FIG. 2, two plane-parallel elements, a plate 6 and an element 7, are provided that limit the subject 1 to be examined in two directions in two planes aligned essentially parallel to one another. The element 7 is transparent for ultrasound waves, whereas the plate 6 reflects ultrasound waves. Plate 6 and element 7 are connected to one another with an axial adjustment mechanism 8. The spacing between the element 7 and the plate 6 can be individually set with adjustment elements 9 and 10. The following spatial directions are employed for the following description: x forms the penetration direction of the ultrasound signals and, thus, the t-axis for the ultrasound echoes received in chronological succession. The y-axis forms a first "motion" axis in the signal pick-up and, thus, the second coordinate for the illustration of a tomogram. The z-axis then forms the secondary motion axis of the signal pick-up and thus enables the generation of a three-dimensional image. The "motion", however, need not ensue mechanically but can be undertaken by electronic scanning a linear or planar transmitter/receiver array.

The primary wave transmitter/echo signal receiver 2 is arranged mounted in a carriage 12 so as to be movable along the longitudinal axis of the carriage 12 and lockable in a selected position along the longitudinal axis. The carriage 12 is likewise connected to cross-rods 11 of the adjustment mechanism 8 in this preferred embodiment of the apparatus. The carriage 12 is in turn displaceable along the longitudinal axis of the cross-rods 11. The primary wave transmitter/echo signal receiver 2, which lies against the outside of the element 7, can move over the entire planar surface of the element 7 with the carriage 12 for scanning the subject 1 to be examined. The respective position, i.e. the spatial direction of the primary wave transmitter/echo signal receiver 2 can be set either manually or driven by a stepping motor or with electronic scan means.

The respective edges 13 and 14 of the plate 6 and of the element 7 lying against the human body is anatomically rounded, i.e. in particular, concave.

This preferred exemplary embodiment is especially simple in mechanical terms because an examination subject 1 having an arbitrary shape can be surrounded at any time by a flexible, sealed container 15 that contains a coupling medium 17 and which is transmissive for the (wave) radiation employed. The container 15 is filled and respectively, emptied via a filling nozzle 16. In addition, the coupling medium must thereby merely be applied to the plate 6 and to the element 7 in order to assure that the wave radiations can be well-transmitted.

In the illustrated exemplary embodiment of the inventive apparatus, the reflective plate 6 simultaneously forms a reception means for a further imaging signal effective in a parallel spatial direction or forms a receptacle for such a reception means.

The examination method includes producing a further image of the subject by x-ray examination or by digital radiography of the subject retained in identical position as for the ultrasound examination. Further information with respect to the detected inhomogeneity can thus be acquired with an advantageous reduction of the x-ray load by comparison to techniques requiring x-ray exposures from two different spatial directions that are currently standard. The x-ray tube can thereby temporarily take the place as warranted of the ultrasound transmission and reception means.

The X-radiation is indicated by the ray beam 21 that transirradiates the subject 1 and reaches the X-ray film that is arranged in a cassette. The upper cover surface of the cassette 23, in particular, is identical to the plate 6 that serves as the reflection surface for the ultrasound examination. In an indicated, alternative embodiment, a thermally sensitive surface for a thermography method is located at the upper side of the plate 6 and is indicated with a broken line.

The subject 1 to be examined is thereby fixed with the adjustment unit 8 and adjustment elements 9 and 10 and the primary radiation signals 3 emitted by the primary wave transmitter/echo signal receiver 2 are reflected by the plate 6, after passing through the subject 1, as echo signals 4, and are picked up by the primary wave transmitter/echo signal receiver 2. The transit times and the amplitudes of the echo signals 4 are thereby registered for the different spatial directions 5 of the emitted primary radiations 3 by the evaluation means connected to the primary wave transmitter/echo signal receiver 2.

With the subject in the same position, an image presentation superimposed on the first is subsequently (or, potentially, simultaneously) generated with the second imaging examination method, thereby obtaining data supplementing the previously registered geometrical data in the identical position. In particular, the coupling medium 17 is selected such that its attenuation or influencing for the imaging radiation corresponds to the properties of normal tissue, so that it appears neutral in the image display.

Alternatively, the further information can be obtained thermographically or by diaphanography, whereby the illumination source coincides with the source 20 in the latter instance.

In particular, the information obtained by X-radiation can be directly digitally recorded or can be subsequently digitized—preferably by scanning—from an X-ray exposure obtained in the usual way.

The signal curves that arise at boundaries of inhomogeneities and the signal curves arising therefrom shall now be discussed in greater detail with reference to FIGS. 3a–3d and 4a–4d.

The sectional views according to FIGS. 3a–3d show various inhomogeneities upon transirradiation with ultrasound (in the x-direction) for explaining inventive method. The spatial direction of the primary radiation is respectively indicated by the direction of the arrow, whereby the degree of shading of the illustration indicates the number or the intensity of the echoes obtained. The signal 25 obtained by the additional imaging method is thereby reproduced as a sectional view extending horizontally in FIGS. 3a through 3d respectively below the ultrasound image. This shows how the shading arises as an indication of malignant tissue in a conspicuous region in the ultrasound signal. The illustration, however, can thereby only be schematic. In particular, an electronic further processing of the signals is thereby assumed, whereby an inversion was undertaken compared to the presentation on an X-ray film.

Figure 3A:
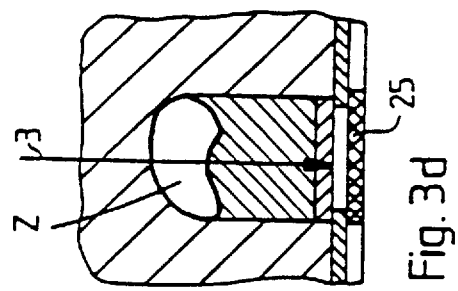
FIGS. 3a–3d are schematic views of tissue inhomogeneities which become apparent upon insonification of the subject in accordance with the inventive method, shown in section.

FIG. 3a shows a tumor-free subject containing fatty tissue F and glandular member DK. The fatty tissue F has a lower echo density than the glandular member DK, and the ultrasound-reflective plate P has the highest echo density.

Figure 3B:
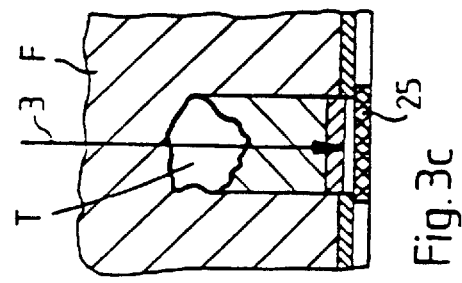

FIG. 3b shows a subject having a malignant tumor T. The malignant tumor appears nearly without echo and with a bilateral edge shadow behind the tumor.

Figure 3C:
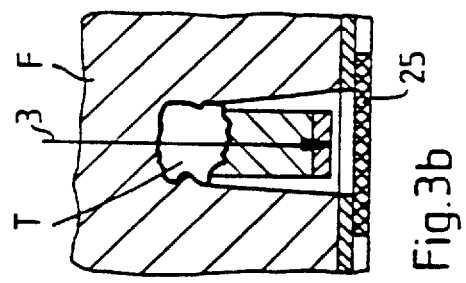

FIG. 3c shows a subject having a malignant tumor T. The malignant tumor appears nearly without echo but, by contrast to FIG. 3b has a moderate central shadow behind the tumor.

Figure 3D:
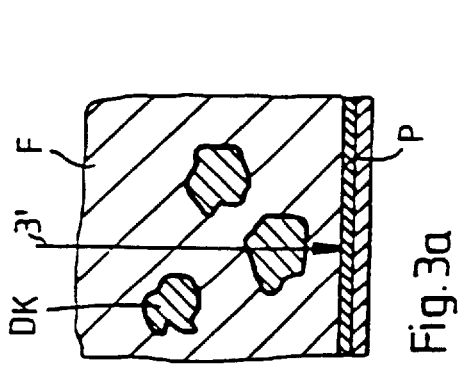

FIG. 3d shows a subject having a benign cyst Z. Like most cysts, the cyst Z appears without echoes and with a central sound intensification behind the cyst.

The various echo signal curves arising from FIGS. 3a–3d are respectively additionally shown in FIGS. 4a–4d (t-axis, corresponding to the x-direction). The additional image portions of an imaging method such as fluoroscopy do not appear in these illustrations. The additional imaging method thus contains no "depth information" since it is based on fluoroscopy. The same is also true, however, for the other signals "plate shift" and "plate absence" obtained from the ultrasound examination, which likewise contain no spatial information.

Figure 4A:
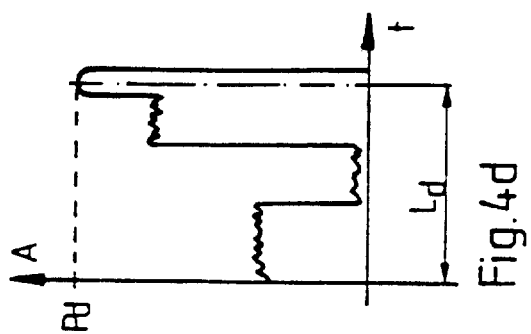
FIGS. 4a–4d illustrate echo signal curves respectively corresponding to the views according to FIGS. 3a–3d.

FIG. 4a shows the echo signal curve of the reference primary radiation 3' that passes through the tumor-free subject containing fatty tissue F and glandular member DK. The variations in the echo amplitude A with the time t and, therefore, with increasing distance from the primary radiation transmitter/echo signal receiver are thereby entered. The fatty tissue F has a lower amplitude than the glandular member DK, whereby the region of the highest amplitude values $P_a$ indicates the position of the ultrasound-reflective plate.

Figure 4B:
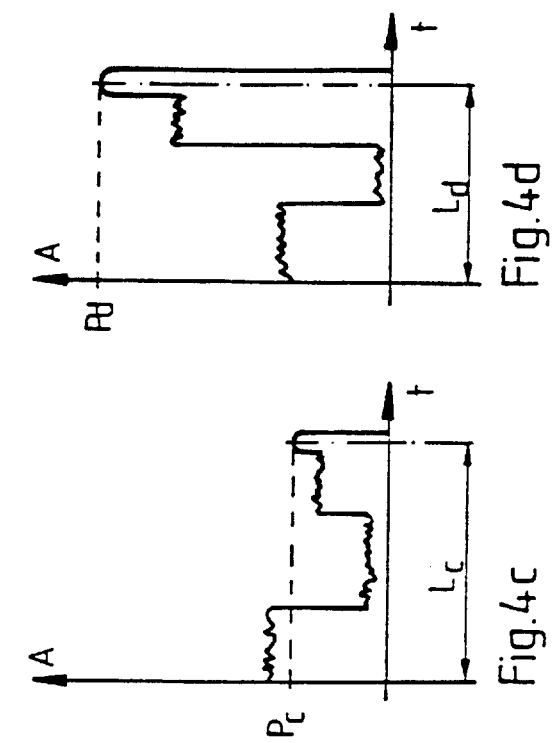

FIG. 4b shows the echo signal curve of a primary radiation 3 passing through the malignant tumor T. The amplitude in the region of the tumor T and of the bilateral edge shadow is thereby substantially lower than that of the surrounding fatty tissue F. It can also be seen that the transit time $L_b$ up to the region of the increased amplitude values $P_b$ of the plate has shortened in comparison to the transit time $L_a$ of the echo signal according to FIG. 4a but that the increased amplitude values $P_b$ are lower than the increased amplitude values $P_a$ of the echo signal curve according to FIG. 4a. The shortening of transit time thereby presents itself as an apparent plate deformation.

Figure 4C:
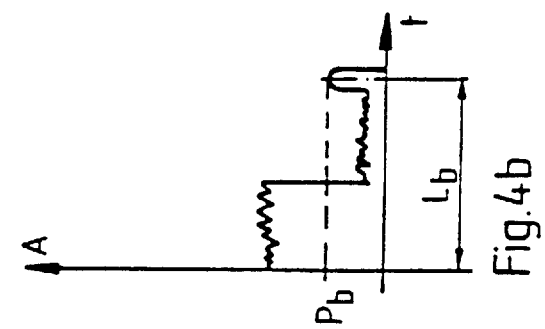

FIG. 4c shows the echo signal curve of a primary radiation signal 3 passing through the malignant tumor T. The amplitude in the region of a tumor T is significantly lower than that of the surrounding fatty tissue F and the moderate central shadow has a reduced amplitude compared to the amplitude in front of the tumor T. As can be seen in the same way as in FIG. 4b, the transit time $L_c$ up to the region of increased amplitude values $P_c$ of the plate has shortened in comparison to the transit time $L_a$ of the echo signal according to FIG. 4a and that the increased amplitude values $P_c$ are lower than the increased amplitude values $P_a$ of the echo signal curve according to FIG. 4a.

Figure 4D:
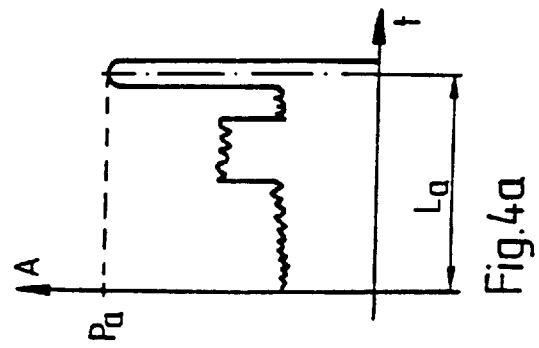

FIG. 4d shows the echo signal curve of a primary radiation signal 3 that passes through the benign cyst Z. The amplitude in the region of the cyst Z is essentially equal to zero and the central sound intensification having an amplitude following the cyst Z that is increased compared to the amplitude preceding the cyst Z may be seen. As can also be seen the transit time $L_d$ up to the region of the increased amplitude values $P_d$ of the plate 6 has in fact shortened in comparison to the echo signal curve according to FIG. 4a, but the increased amplitude values $P_d$ essentially continue to exceed the increased amplitude values $P_a$ of the echo signal curve according to FIG. 4a.

By repeated scanning of the subject in further planes directed perpendicularly relative to the first plane, a three-dimensional image can be produced in a further exemplary embodiment (not shown here) by means of combining the identified echo signal curves by superimposition.

In order to be able to distinguish a benign inhomogeneity that shortens the transit time of the echo signals from a malignant inhomogeneity even better, the ultrasound image of the reflective plate 6 is three-dimensionally shown in FIG. 5. The spatial contour of the region in which an inhomogeneity is expected with high probability can thus be graphically reproduced. The nature of the edge contour of the distorted region of the reflective plate 6 can thus be seen, enabling a conclusion about the nature of the edge contour of the inhomogeneity. Studies have shown that malignant findings usually have irregular edge contours, whereas benign findings have smooth edge contours. By retrieving the primary image directed parallel to the direction of acoustic propagation, further, the inhomogeneity causing a disturbance is directly accessible for observation, so that a more detailed characterization is possible.

The three-dimensional illustration according to FIG. 5 shows the ultrasound-reflective plate 6 given the presence of a malignant tumor in the subject to be examined. The irregular nature of the contour of the region of the plate 6 displayed distorted can be clearly recognized. In FIG. 5 the illustration is supplemented by a second diagram obtained from the second imaging method. This is again a presentation obtained with X-radiation. It can be seen with reference to the nature of the edge contour that there is a high probability of a malignant finding. Further, a spatially limited region of the body part under examination wherein the malignant finding can be found with high probability can be identified by the projection of the region displayed distorted in the direction of the upper wave-transmissive element.

Figure 6:
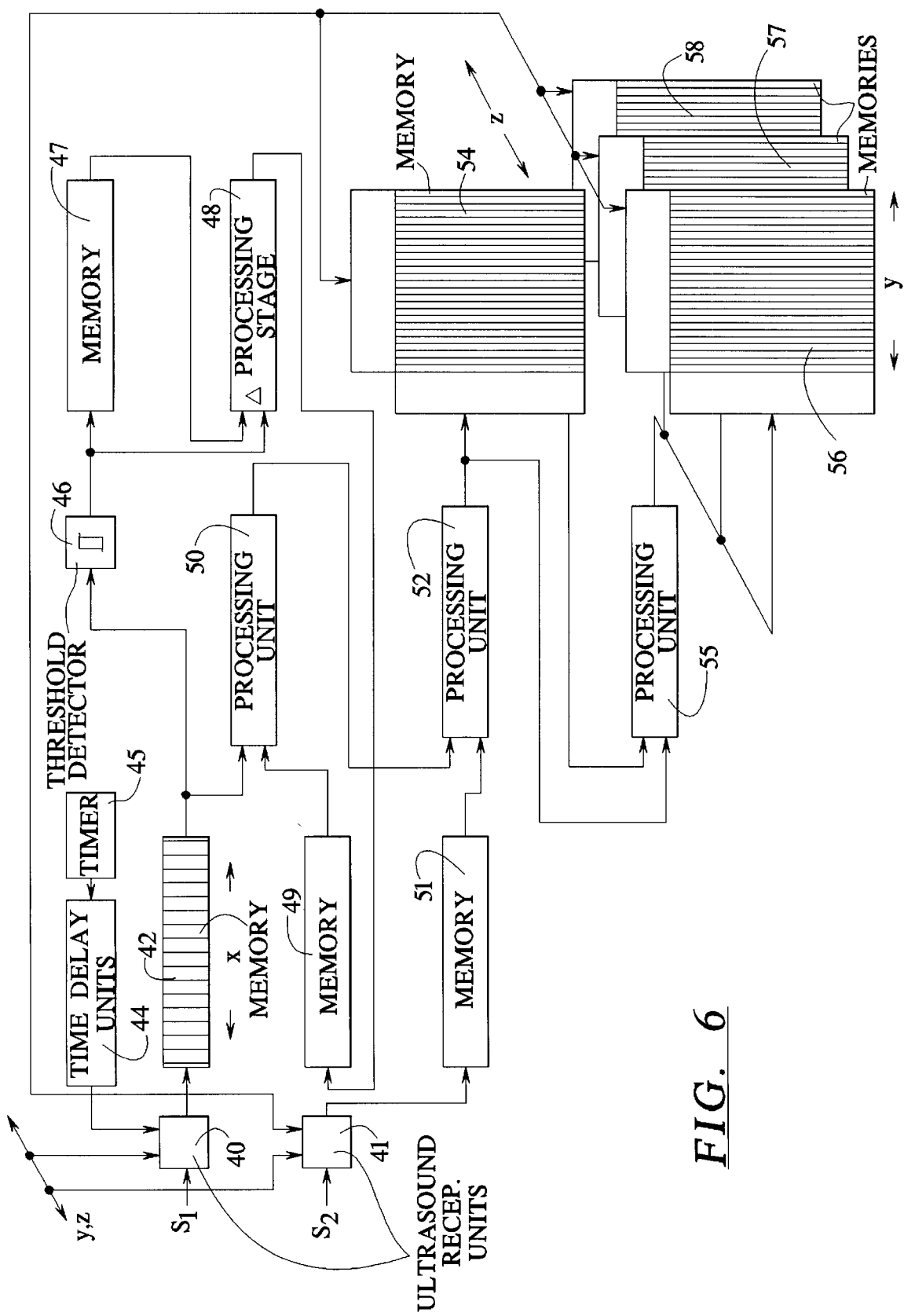
FIG. 6 is a block circuit diagram of a processor system for signal processing constructed in accordance with the principles of the present invention and operating according to the inventive method.

Given the fundamental structure of an evaluation means for the inventive method shown in the form of a block circuit diagram in FIG. 6, the ultrasound echoes $S_1$ picked up by an ultrasound reception unit 40 are written into a memory 42 as digitized amplitude signals. The memory 42, for example, may be formed by a shift registered for the acceptance of the digitized signals. A further reception unit 41 serves the purpose of receiving another spatially correlated, imaging signal obtained from the organ under examination that shall be set forth in greater detail below. The signal present in the shift register memory 42 constitutes the digitized amplitude values of the received echo, whereby the reception is started after receipt of an output signal of a time delay means 44 that defines the point in time of emission of the ultrasound signals, this time delay means 44 having in turn been activated by a timer 45. The returning signal is thus retained in the memory 42 in response to every ultrasound signal pulse that is emitted, whereby the digitized representation in the x-direction (penetration depth) corresponds to that of FIGS. 4 and 5.

The sound reception unit 40 is positioned in different positions with reference to the organ under examination, by means of an apparatus for line-by-line linear shift in the y-direction (see FIG. 3) that is preferably automated. A line-by-line scanning for slice-by-slice presentation of the organ to be examined or the body part to be examined is thus possible. In a modification of the invention (not shown here), the line-by-line scanning can alternatively ensue by simultaneous pick-up of a respective, entire line with a corresponding array of ultrasound transmitters/receivers.

The exemplary embodiment shown in FIG. 6 represents the evaluation circuit for the signals successively registered within a spatial plane, i.e. for a two-dimensional region. An ultrasound transmitter/receiver that emits signals simultaneously for an entire slice is required for a simultaneous two-dimensional acquisition, whereas such an arrangement would have to be correspondingly multiplied for every further slice to be acquired given a three-dimensional acquisition. This leads to a planar-like array arrangement for the ultrasound transmitters/receivers.

Even when undertaking a scanning sampling of the signals registered without mechanical motion, however, the further-processing thereof is ultimately repetitively undertaken, thus the operating mode in the acquisition of the individual, geometric planes is a corresponding, so that a processing conforming to the following description also ensues.

Upward transgressions of a predetermined threshold in the echo signal that are received and identified digitized in the shift register 42 and that exceed the amplitudes of echoes of body tissue and form echoes of the highly reflective plate are retained with a threshold detector 46. This value is written into an average value or reference value memory 47 wherein the chronological averages of the amplitudes and/or echo delays, or the delay times of the majority of the registered echo delay times of the pulses exceeding the threshold are written. In another version of the illustrated exemplary embodiment, the reference value can alternatively be a permanently prescribed value that is obtained on the basis of empirical values or that were calculated from the known geometry of the arrangement.

In a further processing stage 48, the difference of the echo time of the registered pulse since the emission thereof or its amplitude is calculated and is compared to the reference value contained in the memory 47 and is forwarded to a memory 49 for the shift of the echo of the plate that is "hard" with respect to the reflection properties or of the reduction of the echo amplitude due to subject located in the intervening body tissue. This virtual plate deformation or "echo reduction"—as set forth—forms a further local, characteristic signal for a point of the x, y-plane as an indication for the presence of malignant tissue but without information in the x-direction. The obtained values are retained in the memory 49. In a first processing unit 50, the signal contained in the memory 49 is attached to the output signal of the shift register 42 as further information. This can ensue in a simple way by retaining the value of the echo shift or echo reduction in an additional memory cell provided for that purpose.

A further imaging signal that is characteristic of the corresponding point in the x, y-plane and that is emitted by the signal pick-up 41 and retained in a memory 51 is, as warranted, attached, in a second processing unit 52, to the output signal of the first processing stage 50. This signal is then likewise carried along in the signal respectively corresponding to a point of the display in the y,z-plane.

This signal is deposited in a memory 54, which is organized matrix-like and which accepts the entire echo signal (x-axis information) including the aforementioned auxiliary signals for a y-scan line.

In a third processing unit 55, the aggregate signal obtained for a point of the y-axis is now correlated with further signals that were registered at an earlier point in time.

These further signals are preferably signals extending along the z-direction so that a conclusion about the tumor probability for a slice of the tissue under observation is obtained from the superimposition of the local depth echo (x-direction), of the local echo shift, the local signal of a further imaging method and the corresponding, neighboring signals in z-direction, this being compared to the current signal or being correlated in some other way. Signal modifications compared to neighboring signals can thus also enter into the locally registered signal.

Further, correspondingly processed slice images are obtained by further signal pick-up given a shift in the z-direction, the further slice images being deposited in further memories 56–58 (only shown by way of example), so that a three-dimensional image that can be interpreted overall is obtained with the combined content of these memories. The correlation of the contents of neighboring memory locations in the z-direction likewise forms a possibility of improving the obtained information further, as was already shown with reference to the example of the third processing unit 55. Correspondingly, a correlation of images registered from different spatial directions can also ensue. In the case of examinations of the female breast, however, the spatial arrest thereof is a prerequisite for the signal calculation from different spatial directions.

The implementation of the invention is not limited to the preferred exemplary embodiment recited above. On the contrary, numerous modifications are conceivable that make use of the illustrated solution even given fundamentally differently constituted embodiments.

Although modifications and changes may be suggested by those skilled in the art, it is the intention of the inventor to embody within the patent warranted hereon all changes and modifications as reasonably and properly come within the scope of his contribution to the art.

I claim:

1. A method for examining a female mammary gland comprising the steps of:

maintaining a mammary gland in a fixed position;

introducing primary ultrasound radiation into said mammary gland along a selected spatial direction while said mammary gland is in said fixed position, said primary ultrasound radiation being reflected by said mammary gland and thereby producing echo signals at respective locations within said mammary gland;

receiving said echo signals, each received echo signal having echo signal parameters associated therewith;

displaying said echo signals dependent on at least one of said echo signal parameters in a presentation identifying an origination of said echo signals within the mammary gland relative to a selected spatial orientation reference, said presentation containing information about said mammary gland;

obtaining further signals from said mammary gland produced by a technique selected from the group consisting of x-ray radiography, thermography and diaphanography, with said mammary gland maintained in said fixed position; and displaying said further signals in said presentation, using said spatial orientation reference, together with said echo signals, said further signals containing further information about said mammary gland, at least some of said further information being different from said information in said presentation of said echo signals.

2. A method as claimed in claim 1 wherein the step of maintaining said mammary gland in a fixed position comprises holding said mammary gland between two substantially parallel plates.

3. A method as claimed in claim 1 wherein the step of obtaining further signals from said mammary gland comprises obtaining further signals from said mammary gland by x-ray radiography, and wherein the step of obtaining further signals from said mammary gland by x-ray radiography comprises:

emitting x-rays into said mammary gland, said mammary gland attenuating said x-rays and thereby producing attenuated x-rays; and directly digitally recording said attenuated x-rays.

4. A method as claimed in claim 1 wherein the step of obtaining further signals from said mammary gland comprises obtaining further signals from said mammary gland by x-ray radiography, and wherein the step of obtaining further signals from said mammary gland by x-ray radiography comprises:

emitting x-rays into said mammary gland, said mammary gland attenuating said x-rays and thereby producing attenuated x-rays;

producing an x-ray exposure from said attenuated x-rays; and digitizing said x-ray exposure.

5. A method as claimed in claim 1 wherein the step of displaying said further signals in said presentation together with said echo signal comprises superimposing said further signals on said echo signals for identifying a high probability location of a tumor in said mammary gland as said further information.

6. A method as claimed in claim 1 wherein the step of displaying said further signals in said presentation together with said echo signals comprises conducting a logic operation on said echo signals and said further signals to obtain a logic result indicative of a high probability location of a tumor in said mammary gland, and displaying said logic result as said further information.

7. A method as claimed in claim 1 wherein the step of introducing primary ultrasound radiation into said mammary gland comprises introducing primary ultrasound radiation into a mammary gland from an ultrasound source, and wherein the step of obtaining further signals from said mammary gland comprises obtaining further signals from said mammary gland using an examination field originating from a field source, and wherein said method comprises the additional step of disposing said ultrasound source and said field source at a same side of said mammary gland in a known spatial relationship between said ultrasound source and said field source.

8. A method as claimed in claim 1 wherein the step of introducing primary ultrasound radiation into said mammary gland comprises emitting said primary ultrasound radiation continuously into said mammary gland.

9. A method as claimed in claim 1 wherein the step of introducing primary ultrasound radiation into said mammary gland comprises the steps of:

generating said primary ultrasound radiation in an ultrasound source; and mechanically moving said ultrasound source relative to said mammary gland through a plurality of substantially equidistantly spaced positions for introducing said primary ultrasound radiation into said mammary gland along a plurality of parallel spatial directions.

10. A method as claimed in claim 1 wherein the step of introducing primary ultrasound radiation into said mammary gland comprises the steps of:

generating said primary ultrasound radiation in an ultrasound array having a plurality of individually activatable transducer elements, each transducer element emitting said primary ultrasound radiation along a different spatial direction, said different spatial directions being parallel; and simultaneously activating all of said transducer elements for conducting a scan of said mammary gland.

11. A method as claimed in claim 1 wherein the step of introducing primary ultrasound radiation into said mammary gland comprises the steps of:

generating said primary ultrasound radiation in an ultrasound array having a plurality of individually activatable transducer elements, each transducer element emitting said primary ultrasound radiation along a different spatial direction, said different spatial directions being parallel; and successively activating respective transducer elements for scanning said mammary gland.

12. A method as claimed in claim 1 wherein said mammary gland has a first ultrasound reflectivity associated therewith, wherein the step of maintaining said mammary gland in a fixed position comprises clamping and spatially fixing said mammary gland between a plate element and a reference surface parallel to the plate element, the reference surface having a second ultrasound reflectivity associated therewith which is higher than said first ultrasound reflectivity and said plate element being ultrasound transparent;

wherein the step of introducing primary ultrasound radiation into said mammary gland comprises emitting ultrasound signals into said mammary gland along said selected spatial direction, said selected spatial direction comprising an axis perpendicular to said reference surface, said ultrasound signals proceeding through said plate element and said mammary gland to said reference surface and said mammary gland and said reference surface thereby producing said echo signals, each of said echo signals having echo signal parameters associated therewith comprising a transit time along said axis and an amplitude;

and wherein the step of displaying said echoes dependent on at least one said echo signal parameters in a presentation comprises the steps of:

identifying at least one reference parameter comprising at least one of said echo signal parameters for a reference echo signal passing through said body portion and reflected from said reference surface;

identifying at least one of said echo signal parameters for each echo signal upon reception of the respective echo signals;

identifying a deviation from said at least one reference parameter of the at least one echo signal parameter identified for each signal upon reception of the echo signal; and identifying a probability of the presence of a tumor in said mammary gland dependent on said deviation, as a part of said information about said mammary gland contained in said presentation.

13. An apparatus for examining a female mammary gland comprising:

means for maintaining a mammary gland in a fixed position including first and second plates disposed on opposite sides of said mammary gland, said first plate being ultrasound transparent;

means for introducing primary ultrasound radiation into said mammary gland along a selected spatial direction proceeding through said first plate and said mammary gland while said mammary gland is in said fixed position, said primary ultrasound radiation being reflected by said mammary gland and thereby producing echo signals at respective locations within said mammary gland;

means for receiving said echo signals, each received echo signal having echo signal parameters associated therewith;

means for displaying said echo signals dependent on at least one of said echo signal parameters in a presentation identifying an origination of said echo signals within the mammary gland relative to a selected spatial orientation reference, said presentation containing information about said mammary gland;

means for obtaining further signals from said mammary gland selected from the group consisting of means for conducting x-ray radiography of said mammary gland, means for conducting thermography of said mammary gland and means for conducting diaphanography of said mammary gland, with said mammary gland maintained in said fixed position; and means for displaying said further signals in said presentation, using said spatial orientation reference, together with said echo signals, said further signals containing further information about said mammary gland, at least some of said further information being different from said information in said presentation of said echo signals.

14. An apparatus as claimed in claim 13 wherein said means for introducing primary ultrasound radiation into said mammary gland comprises an ultrasound transmitter, and wherein said means for obtaining further signals from said mammary gland includes a field source which emits an examination field, and wherein said ultrasound transmitter and said field source are disposed at a side of said first plate opposite said mammary gland.

15. An apparatus as claimed in claim 13 wherein said means for introducing primary ultrasound radiation into said mammary gland comprises an ultrasound transducer array, and wherein said ultrasound transducer array is disposed in said first plate.

16. An apparatus as claimed in claim 13 wherein said means for receiving said echo signals comprises an ultrasound transducer array, and wherein said ultrasound transducer array is disposed in said first plate.

17. An apparatus as claimed in claim 13 wherein said means for obtaining further signals from said mammary gland comprises means for conducting x-ray radiography of said mammary gland, said means for conducting x-ray radiography of said mammary gland comprising:

an x-ray source which emits x-rays into said mammary gland, said mammary gland attenuating said x-rays and producing attenuated x-rays; and an x-ray film cassette containing x-ray film disposed in said second plate for photographically registering said attenuated x-rays.

18. An apparatus as claimed in claim 13 wherein said means for obtaining further signals from said mammary gland comprises means for conducting x-ray radiography of said mammary gland, said means for conducting x-ray radiography of said mammary gland comprising:

an x-ray source which emits x-rays into said mammary gland, said mammary gland attenuating said x-rays and producing attenuated x-rays; and an electronic target sensitive to x-rays disposed in said second plate for directly converting attenuated x-rays incident thereon into digital electrical signals.

19. An apparatus as claimed in claim 13 wherein said mammary gland has a first ultrasound reflectivity associated therewith, and wherein said second plate comprises a second plate having a second ultrasound reflectivity associated therewith, said second ultrasound reflectivity being higher than said first ultrasound reflectivity.

20. An apparatus as claimed in claim 13 wherein said means for maintaining said mammary gland in a fixed position comprises means for connecting said first and second plates and for selectively adjusting a spacing between said first and second plates.

* * * * *